United States Patent
Okuda

(10) Patent No.: US 12,256,991 B2
(45) Date of Patent: Mar. 25, 2025

(54) OPHTHALMOLOGIC APPARATUS AND COVER

(71) Applicant: TOPCON CORPORATION, Tokyo (JP)

(72) Inventor: Youki Okuda, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 574 days.

(21) Appl. No.: 17/577,862

(22) Filed: Jan. 18, 2022

(65) Prior Publication Data

US 2022/0233068 A1    Jul. 28, 2022

(30) Foreign Application Priority Data

Jan. 22, 2021  (JP) .................. 2021-008402

(51) Int. Cl.
*A61B 3/00* (2006.01)
*A61B 3/14* (2006.01)
*A61B 3/18* (2006.01)

(52) U.S. Cl.
CPC .............. *A61B 3/0075* (2013.01); *A61B 3/14* (2013.01); *A61B 3/18* (2013.01)

(58) Field of Classification Search
CPC ........... A61B 3/0075; A61B 3/14; A61B 3/18; A61B 3/152; A61B 3/12; A61B 3/0083

(Continued)

(56) References Cited

U.S. PATENT DOCUMENTS 5,071,246 A * 12/1991 Blaha .................. A61B 3/1225
                                                    351/205
8,534,836 B2 * 9/2013 Inoue ...................... A61B 3/12
                                                    351/208

(Continued)

FOREIGN PATENT DOCUMENTS

CN     109350007     2/2019
JP     3-500131      1/1991

(Continued)

OTHER PUBLICATIONS

Extended European Search Report issued Jun. 3, 2022 in corresponding European Patent Application No. 22152676.7.

(Continued)

*Primary Examiner* — Mohammed A Hasan
(74) *Attorney, Agent, or Firm* — WENDEROTH, LIND & PONACK, L.L.P.

(57) ABSTRACT

An ophthalmologic apparatus includes a device body having an eye information acquisition unit including an objective optical system configured to acquire information of a subject's eye, a drive unit configured to move the eye information acquisition unit relative to the subject's eye in upward-downward, rightward-leftward, and forward-rearward directions, and a control unit configured to control the eye information acquisition unit and the drive unit and a casing covering the device body and having an opening provided with a cover configured to cover the opening, and the cover includes a first cover portion movable to the casing in the upward-downward and rightward-leftward directions, being disposed in the opening not to move in the forward-rearward direction and a second cover portion attached to an outer periphery of the objective optical system and inserted into the first cover portion, being movable to the first cover portion in the forward-rearward direction.

7 Claims, 7 Drawing Sheets

(58) Field of Classification Search
USPC .......................................................... 351/205
See application file for complete search history.

(56) References Cited

U.S. PATENT DOCUMENTS

| | | | | |
|---|---|---|---|---|
| 2004/0044333 | A1* | 3/2004 | Sugiura | A61F 9/00817 606/4 |
| 2007/0146535 | A1* | 6/2007 | Nanjo | A61B 3/14 348/78 |
| 2008/0231806 | A1* | 9/2008 | Nakazawa | A61B 3/107 351/212 |
| 2009/0091828 | A1 | 4/2009 | Fukuyama et al. | |
| 2015/0085252 | A1 | 3/2015 | Fujimura et al. | |
| 2016/0309997 | A1* | 10/2016 | Imamura | A61B 3/14 |
| 2016/0345822 | A1 | 12/2016 | Fujimura et al. | |
| 2022/0160230 | A1 | 5/2022 | Kook | |

FOREIGN PATENT DOCUMENTS

| | | |
|---|---|---|
| JP | 9-131315 | 5/1997 |
| JP | 2006-301540 | 11/2006 |
| JP | 2010-17279 | 1/2010 |
| JP | 2013-248376 | 12/2013 |
| WO | 90/00028 | 1/1990 |
| WO | 2020/209418 | 10/2020 |

OTHER PUBLICATIONS

Office Action issued Jul. 3, 2024 in corresponding Japanese Patent Application No. 2021-008402, with English translation.

* cited by examiner

OPHTHALMOLOGIC APPARATUS AND COVER

CROSS-REFERENCE TO RELATED APPLICATION

The present application is based on and claims a priority benefit of Japanese patent application No. 2021-008402, filed on Jan. 22, 2021, the disclosure of which is hereby incorporated herein by reference in its entirety.

FILED OF THE INVENTION

The present invention relates to an ophthalmologic apparatus and a cover.

BACKGROUND

A known ophthalmologic apparatus provided with an optical system including an objective lens is configured to acquire information of a subject's eye with an eye information acquisition unit that acquires information of the subject's eye by moving the eye information acquisition unit up and down, from side to side, and back and forth to align the eye information acquisition unit relative to the subject's eye (see, for example, JP 2010-17279 A). In an ophthalmologic apparatus disclosed in JP 2010-17279 A, a device body including an eye information acquisition unit (optical system unit) is covered with a cover. Inside this cover, the eye information acquisition unit moves up and down, from side to side, and back and forth, and the eye information acquisition unit acquires information of a subject's eye through an opening (imaging window) disposed in the cover.

However, when acquiring information of a subject's eye by the technique in the related art, a subject visually recognizes through the opening that the eye information acquisition unit is moving, particularly, that the eye information acquisition unit is moving forward and approaching the subject' eye. Therefore, the subject may feel a sense of fear that an "object" is closing in on the subject' eye and the subject may not be able to concentrate on the examination. Furthermore, for example, the subject may put a finger from the imaging window by mistake, or dirt, dust, and foreign matters may enter the imaging window.

The present invention has been made in light of the above problems, and an object of the present invention is to hide the movement of an eye information acquisition unit appropriately and to acquire information of a subject's eye appropriately.

SUMMARY OF THE INVENTION

In order to achieve the above-noted object, an ophthalmologic apparatus according to an embodiment of this disclosure includes: a device body; and a casing covering the device body. The device body includes: an eye information acquisition unit including an objective optical system that opposes a subject's eye of a subject, being configured to acquire information of the subject's eye; a drive unit configured to move the eye information acquisition unit relative to the subject's eye in upward-downward direction, rightward-leftward direction, and forward-rearward direction perpendicular to each other; and a control unit configured to control the eye information acquisition unit and the drive unit. The casing includes an opening on one surface opposing the subject's eye, the opening being provided with a cover configured to cover the opening. The cover includes: a first cover portion movable relative to the casing in the upward-downward direction and the rightward-leftward direction, being disposed in the opening not to move in the forward-rearward direction; and a second cover portion attached to an outer periphery of the objective optical system and inserted into the first cover portion, being movable relative to the first cover portion in the forward-rearward direction.

DETAILED DESCRIPTION

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

First Embodiment

Figure 1:
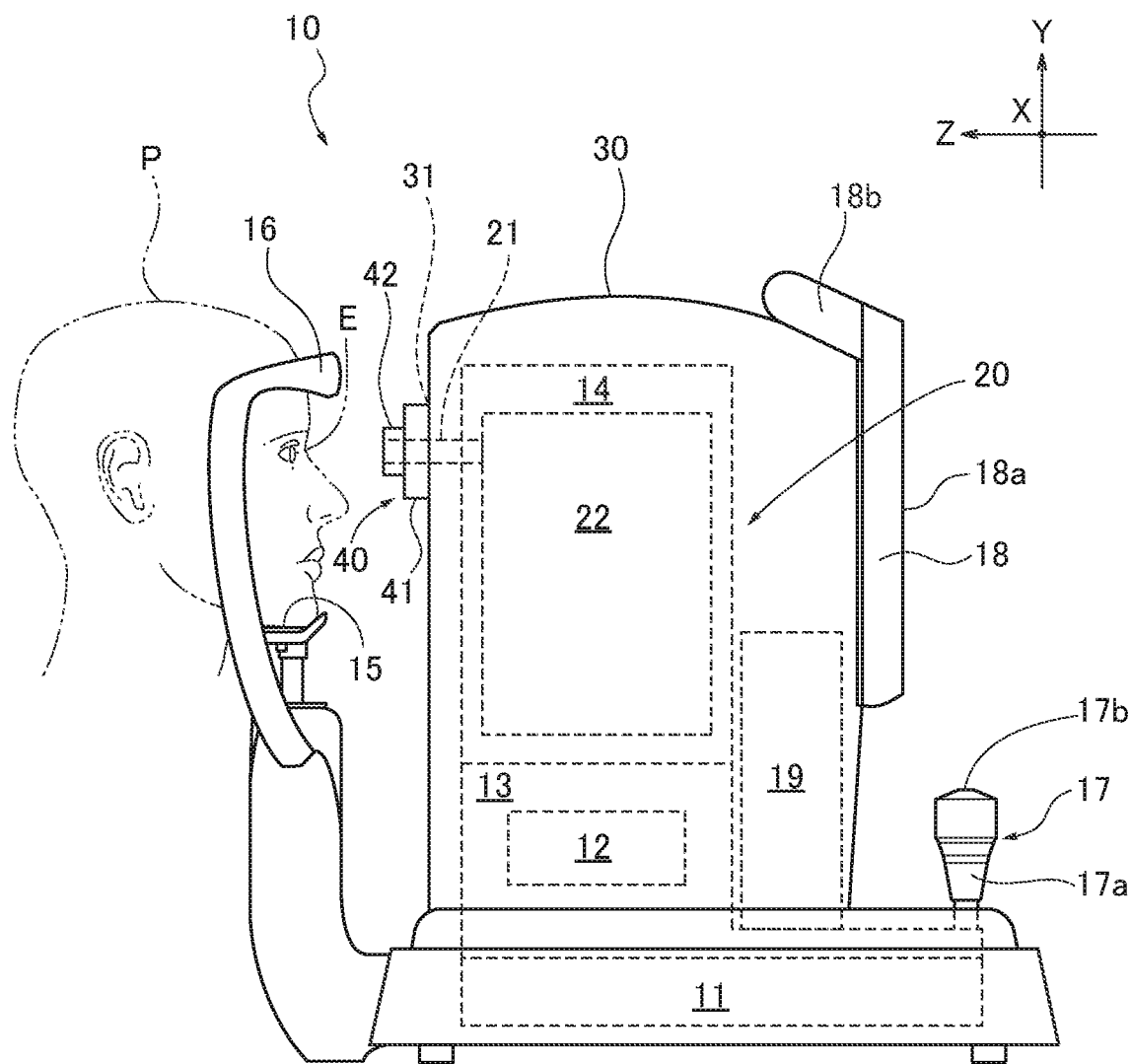
FIG. 1 is a side view illustrating an external appearance of an ophthalmologic apparatus according to a first embodiment of this disclosure.

Hereinafter, an ophthalmologic apparatus 10 as an embodiment of this disclosure will be described with reference to the drawings. FIG. 1 is a side view illustrating an external appearance of the ophthalmologic apparatus 10 according to this embodiment. Herein, X-axis, Y-axis, and Z-axis are set as illustrated in FIG. 1. As viewed from a subject P's perspective, a direction from side to side is defined as "X direction" (positive direction of X-axis is rightward direction, negative direction of X-axis is leftward direction), a direction from the upper side to the lower side (vertical direction) is defined as "Y direction" (positive direction of Y-axis is upward direction, negative direction of Y-axis is downward direction), and a direction from the front to the back (depth direction of the device body 20, where the side closer to the subject P is the front and the opposite side is the back (rear)) is defined as "Z direction" (positive direction of Z-axis is frontward direction, negative direction of Z-axis is rearward direction). In addition, the front side of the ophthalmologic apparatus 10 (the side closer to the subject P) is defined as the front, and the back side (the side closer to an examiner) is defined as the rear.

The ophthalmologic apparatus 10 of this embodiment is a fundus imaging device for observing the fundus of a subject's eye E and capturing images of the fundus. Note that the ophthalmologic apparatus of this disclosure is not limited to a fundus imaging device and may be, for example, an ophthalmologic apparatus that enables one or both of subjective examination and objective examination (to be described), an optical coherence tomography (OCT) device, an axis length measuring device, or a tonometer.

As illustrated in FIG. 1, the ophthalmologic apparatus 10 of this embodiment includes a device body 20 and a casing (body cover) 30 that covers the device body 20. The device body 20 includes a base 11, a drive unit 12, a mount 13, a measurement head 14 as an eye information acquisition unit, a chin rest 15, a head rest 16, an operation unit 17, a monitor 18, and a control unit (control device) 19. The base 11, the drive unit 12, the mount 13, the measurement head 14, and the control unit 19 of the device body 20 are covered by the casing 30. The chin rest 15, the head rest 16, and the operation unit 17 project outward from the casing 30.

In the ophthalmologic apparatus 10 of this embodiment, the mount 13 is disposed in the base 11 with the drive unit 12 involved, and the drive unit 12 enables the mount 13 to move back and forth and from side to side (in Z direction and X direction) relative to the base 11. The mount 13 is provided with the control unit 19 and the measurement head 14. The measurement head 14 is moved up and down (in Y direction) relative to the mount 13 by the drive unit 12.

In this embodiment, the base 11 is also covered by the casing 30, but the present invention is not limited to the configuration. The casing 30 may be fixed to the base 11 to cover the mount 13, the measurement head 14, the drive unit 12, the control unit 19, and the like on the base 11.

The base 11 is provided with the chin rest 15 and the head rest 16 used for fixing the position of the subject P's face, or the subject's eye E, relative to the measurement head 14 when acquiring eye information. The chin rest 15 and the head rest 16 are moved up and down relative to the base 11 by a known drive unit (or manually). The ophthalmologic apparatus 10 acquires information associated with, for example, observation, imaging, and examination of the subject's eye E while the subject P opposes the measurement head 14, resting his/her head on the head rest 16 and his/her chin on the chin rest 15.

The operation unit 17 is operated when an examiner or the subject P gives the ophthalmologic apparatus 10 instructions such as actions and settings of the chin rest 15, the measurement head 14, and the drive unit 12. The operation unit 17 of this embodiment includes a tiltable control lever 17a disposed on the mount 13. The examiner operates the control lever 17a to move the measurement head 14 three-dimensionally relative to the base 11. Furthermore, the control lever 17a is provided with a button switch 17b at the top. The examiner presses the button switch 17b to start optometry by the measurement head 14.

The operation unit 17 also includes software keys such as control buttons shown on the screen 18a of the monitor 18. Operating the control buttons enables various actions such as alignment relative to the subject's eye E, setting of various examination conditions, and adjustment of the screen 18a. Note that the operation unit 17 may include input devices such as various buttons, a keyboard, and a mouse disposed around the control lever 17a and around the monitor 18.

The monitor 18 is attached to the top of the casing 30. The monitor 18 is, for example, a liquid crystal display (LCD monitor) and includes the screen 18a of touch panel type. Under control of the control unit 19, the monitor 18 appropriately shows, for example, images of the subject's eye E (such as anterior segment images, fundus images, and OCT images) based on image data from the measurement head 14, various kinds of examination information (such as examiner information, examination conditions, examination results, and measurement images) from the measurement head 14, and an image of the control buttons functioning as the operation unit 17. The monitor 18 of this embodiment is rotatably supported by the casing 30 via a rotary support mechanism 18b, and the orientation of the screen 18a can be changed appropriately. For example, the screen 18a can be oriented to the subject, or the screen 18a can be turned sideways (in X direction).

The control unit 19 collectively controls each unit in the ophthalmologic apparatus 10. The control unit 19 includes a CPU and a storage unit such as RAM, ROM, EEPROM, and hard disk drive. To the control unit 19, for example, the drive unit 12, the chin rest 15, the operation unit 17, the monitor 18, the measurement head 14, and the storage unit are connected. The control unit 19 unfolds a computer program stored in the storage unit in advance on, for example, RAM, thereby collectively controlling actions of the ophthalmologic apparatus 10 (drive unit 12, chin rest 15, monitor 18, measurement head 14) according to the operation of the operation unit 17.

The measurement head (eye information acquisition unit) 14 acquires eye information of the subject's eye E. Examples of the eye information include not only anterior segment images of the subject's eye E, fundus images of the subject's eye E, and tomographic images of the retina of the subject's eye E but also corneal endothelial images of the subject's eye E and characteristics of the subject's eye E such as refractive power, corneal shape, and intraocular pressure.

The measurement head 14 includes an objective optical system unit 21 that opposes the subject's eye E and a measurement optical system 22 that includes optical elements such as relay lens, imaging element, eyepiece, and light source. The objective optical system unit 21 includes an objective optical system 21a including at least one objective lens and a lens barrel 21b housing the objective optical system 21a. As illustrated in FIG. 1, the objective optical system unit 21 projects outward from an opening 31 disposed in a casing body in the front of the casing 30 (the side closer to the subject's eye E), which enables the objective optical system 21a to oppose the subject's eye E.

At least one of subjective examination and objective measurement is performed with the measurement head 14. The subjective examination is an approach to acquiring information of the subject's eye E using a response from the subject P. Examples of the subjective examination include perimetry and subjective refractometry such as distance vision test, near vision test, contrast sensitivity test, and glare test. The objective measurement is an approach to acquiring information of the subject's eye E mainly using a physical method without referring to a response from the subject P. The objective measurement includes acquiring characteristics of the subject's eye E and capturing images of the subject's eye E. Examples of the objective measurement include objective refractometry, corneal topography, tonometry, fundus imaging, and optical interferometry. Since the ophthalmologic apparatus 10 of this embodiment is an ophthalmic imaging device, the measurement head 14 mainly captures fundus images.

The objective optical system unit 21 is disposed in the opening 31 of the casing 30, being capable of moving up and down, from side to side, and back and forth. For this reason, the opening 31 has a size that does not prevent the objective optical system unit 21 from moving up and down and from side to side. In other words, a dimension of the opening 31 in the upward-downward direction corresponds to a length obtained by adding outside diameters of the objective optical system unit 21 and a second cover portion 42 (to be described later) that houses the objective optical system unit 21 and a moving distance in the upward-downward direction, and a dimension of the opening 31 in the rightward-leftward direction corresponds to a length obtained by adding the above outside diameters and a moving distance in the rightward-leftward direction.

In the related art, the subject P visually recognizes the measurement head 14 inside the casing 30 through the opening 31 with no cover 40 and sees how the measurement head 14 moves up and down, from side to side, and back and forth. Particularly, the forward movement of the measurement head 14 possibly gives the subject P a sense of fear that the measurement head 14 is approaching. For this reason, the subject P may not be able to concentrate on the examination and may glance away from a target or separate his/her face from the chin rest 15 or the head rest 16, which affects the acquisition of the eye information. In addition, someone may put a finger in the opening 31 by mistake, or dirt, dust, and foreign matters may enter the opening 31. The opening 31 may be covered with a curtain or the like. However, the curtain may be opened along with the movement of the objective optical system unit 21, and it is difficult to appropriately hide the inside of the casing 30.

In order to solve these problems, in the ophthalmologic apparatus 10 of this embodiment, the cover 40 is attached to the opening 31 to close the opening 31 as illustrated in FIGS. 1 and 2A to 2C so that the subject P does not visually recognize the inside of the casing 30.

Figure 2A:
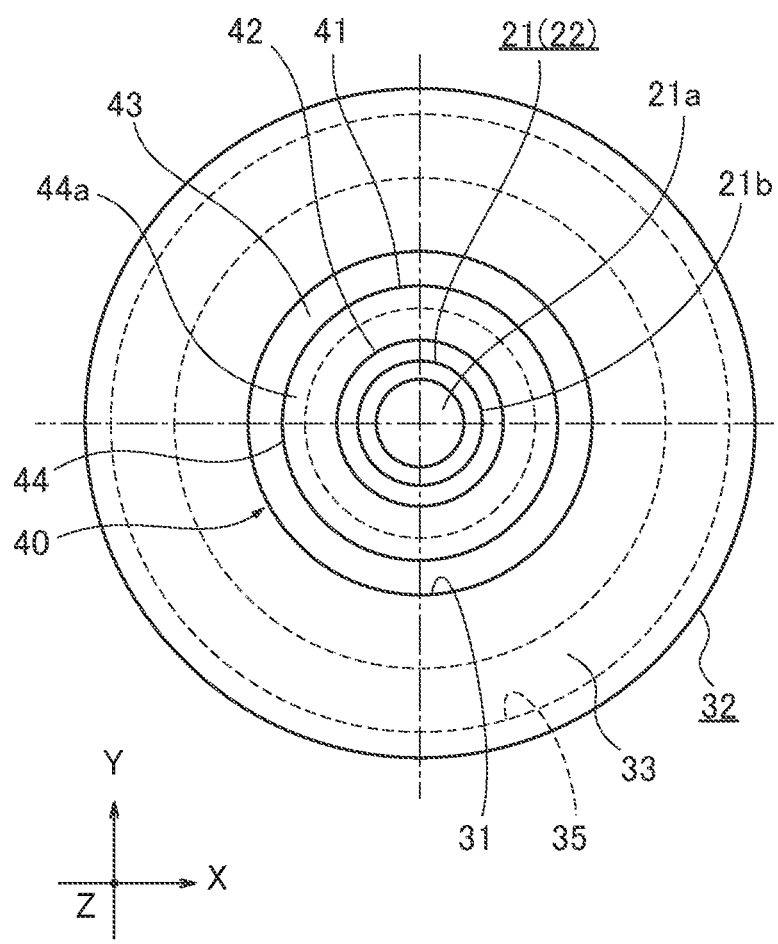
FIGS. 2A to 2C are views for describing configurations of a cover and a casing.
Figure 2B:
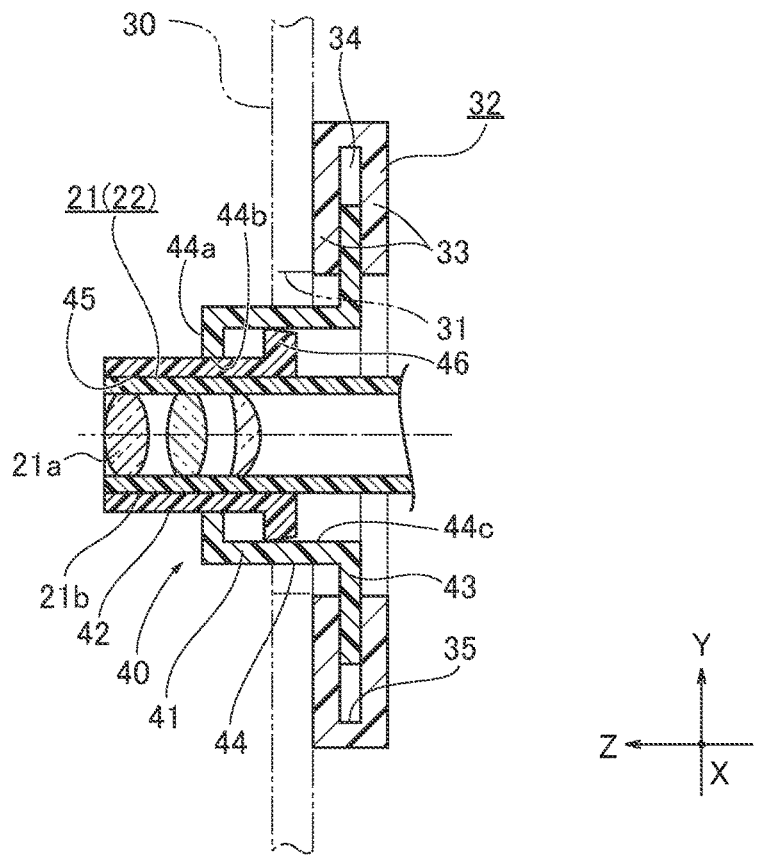
Figure 2C:
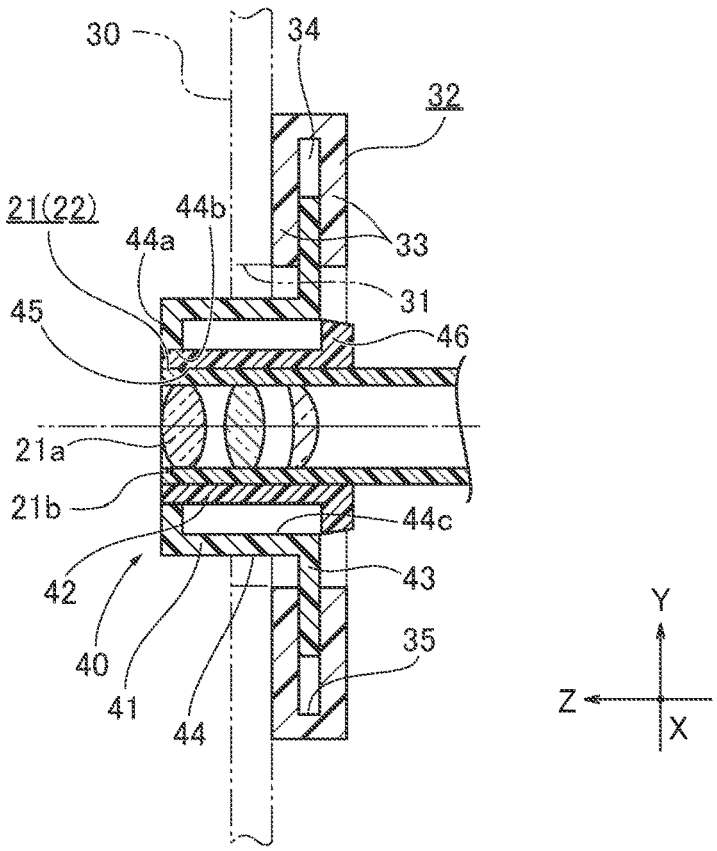

Details of the cover 40 will be described with reference to FIGS. 2A to 2C. FIG. 2A is a front view of the cover 40 and the vicinity of an engagement holder 32 of the casing 30, and FIG. 2B is a side view (cross-sectional view) thereof. FIG. 2C is a side view (cross-sectional view) of the cover 40 moved to a position different from that in FIG. 2B.

As illustrated in FIGS. 2A and 2B, the cover 40 includes a first cover portion 41 disposed in the opening 31 and a second cover portion 42 attached to an outer periphery of the objective optical system unit 21. The first cover portion 41 disposed in the opening 31 is capable of moving up and down and from side to side (rightward and leftward), but not back and forth forward-rearward) relative to the casing 30. The second cover portion 42 is inserted into the first cover portion 41, and is capable of moving back and forth (forward-rearward) relative to the first cover portion 41. In other words, the first cover portion 41 and the second cover portion 42 have a nested structure (telescopic structure).

The first cover portion 41 has a protruding shape in side view, including a disk-shaped base plate 43 disposed in the opening 31 and a cylindrical guide 44 projecting from the base plate 43 toward the subject's eye E (the front).

The base plate 43 functions as a cover of the opening 31 and as an engagement portion with respect to the opening 31. In other words, the base plate 43 engages with the engagement holder 32 disposed along the opening 31 in an inner surface of the casing 30. The engagement holder 32 has a ring shape in plan view and has a U-shape in cross-sectional view, including a pair of holding walls 33 for holding the base plate 43 and a housing space 34 partitioned by the pair of holding walls 33 to house the base plate 43. A distance between inner surfaces of the pair of holding walls 33 (width of the housing space 34) is substantially equal to a thickness of the base plate 43 (length in the forward-rearward direction).

Accordingly, the base plate 43 can freely move up and down and from side to side (that is, in X-Y plane) within the housing space 34 while touching the inner surfaces of the pair of holding walls 33 and closing the opening 31. Simultaneously, the movement of the base plate 43 in the forward-rearward direction is suppressed (blocked). Furthermore, when the first cover portion 41 moves in X-Y plane, an outer peripheral edge of the base plate 43 abuts a bottom face 35 of the housing space 34 or an outer periphery of the guide 44 abuts a peripheral edge of the opening 31, thereby suppressing further movement. Therefore, the engagement holder 32 functions as a movement controller that allows the first cover portion 41 to move up and down and from side to side by a predetermined distance but suppresses the movement of the first cover portion 41 in the forward-rearward direction and functions as a retainer that prevents the cover 40 from coming off the opening 31. In addition, closing the opening 31 by the base plate 43 appropriately prevents penetration of dirt and the like into the casing 30 from the opening 31 and prevents insertion of a finger.

The guide 44 of the first cover portion 41 has a cylindrical shape with both ends opened, including an inward flange 44a projecting toward the center from a peripheral edge of one (front) end opposing the subject's eye E. An inner peripheral edge of the inward flange 44a is an insertion hole 44b through which the second cover portion 42 is inserted.

In this embodiment, the engagement holder 32, a separate member from the casing 30, is fixed to the inner surface of the casing 30, but the present invention is not limited to this configuration. For example, an L-shaped member in cross-sectional view may be fixed to the inner surface of the casing 30, and a wall of this member and a wall of the casing 30 may form an engagement holder. Alternatively, the casing 30 may have a thick wall, and the wall may be hollowed out along an inner periphery of the opening 31 to form a housing space, thereby forming an engagement holder.

The second cover portion 42 is a tubular member with both ends opened (cylindrical member in this embodiment), including a housing space 45 for housing the objective optical system unit 21. In other words, the second cover portion 42 is attached to the outer periphery of the objective optical system unit 21, being capable of moving up and down, from side to side, and back and forth together with the measurement head 14 including the objective optical system unit 21. The second cover portion 42 is inserted into the insertion hole 44b of the guide 44 of the first cover portion 41, being capable of moving back and forth. An inside diameter of the insertion hole 44b and an outside diameter of the second cover portion 42 are substantially equal. While the second cover portion 42 closes the insertion hole 44b, the second cover portion 42 touches an inner surface of the insertion hole 44b and moves back and forth. However, the movement of the second cover portion 42 relative to the first cover portion 41 is suppressed in the upward-downward direction and the rightward-leftward direction.

Therefore, when the measurement head 14 moves back and forth, the second cover portion 42 moves back and forth within the guide 44 of the first cover portion 41 independently from the first cover portion 41. When the measurement head 14 moves up and down and from side to side, the second cover portion 42 moves up and down and from side to side together with the first cover portion 41. In addition, dirt and the like are prevented from penetrating into the casing 30 from the insertion hole 44b.

Furthermore, the second cover portion 42 is provided with an outward flange 46 projecting radially outward from a peripheral edge of the rear end. The outward flange 46 has a dimension large enough to touch a guide surface 44c of the guide 44 of the first cover portion 41. When the second cover portion 42 moves back and forth, the outward flange 46 moves along the guide surface 44c while touching the guide surface 44c. The guide 44 appropriately guides the movement of the second cover portion 42 in the forward-rearward direction, suppresses rattles, vibrations, and the like during the movement, and supports smooth movement of the second cover portion 42.

When the second cover portion 42 moves forward, the outward flange 46 abuts the inward flange 44a of the guide 44 to suppress further movement. Therefore, the outward flange 46 and the inward flange 44a double as a movement controller and as a retainer of the second cover portion 42.

A moving distance of the second cover portion 42 in the forward-rearward direction substantially accords with a moving distance of the measurement head 14 in the forward-rearward direction (operating distance for alignment). When the measurement head 14 moves forward to the maximum extent together with the second cover portion 42, it is desirable that the outward flange 46 abuts the inward flange 44a or is arranged at a position leaving a predetermined margin without abutting the inward flange 44a. On the other hand, when the measurement head 14 moves backward to the maximum extent together with the second cover portion 42 as illustrated in FIG. 2C, it is preferable that one (front) end surface of the first cover portion 41 (more specifically, the guide 44) and one (front) end surface of the second cover portion 42 are flush with each other. In this manner, adjusting the dimension of each member prevents the second cover portion 42 from coming off the first cover portion 41 or coming off the objective optical system unit 21 and prevents influences on the movement of the measurement head 14.

The first cover portion 41 and the second cover portion 42 are not particularly limited in material and may employ a metallic material, a resin material, or the like. However, a resin material is desirable from viewpoints of, for example, cost reduction, enhancement of adhesion between the members, and reduction of noise and abrasion caused by a rub between the members. Examples of the resin material include, but are not limited to, polycarbonate resin, ABS resin, polyacetal resin, and nylon resin.

The first cover portion 41, the second cover portion 42, and even the engagement holder 32 preferably employ, for example, an elastic resin material such as polyurethane resin or polyester resin. Such a resin material enhances the adhesion of a sliding portion, or a contacting portion, between the engagement holder 32 and the first cover portion 41 and a sliding portion between the first cover portion 41 and the second cover portion 42, which further prevents formation of a gap that allows penetration of dust and the like. Even when one of two contacting parts includes an elastic resin material and the other includes a relatively hard resin material, the contacting parts can move smoothly while adhering to each other not to form a gap.

It is also preferable to provide a friction reducer that reduces frictional resistance on the sliding portion (contacting surface) between the engagement holder 32 and the first cover portion 41 and the sliding portion (contacting surface) between the first cover portion 41 and the second cover portion 42. Examples of the friction reducer include fluororesin applied to the surface of each sliding portion (contacting surface) and a fluororesin-processed sheet spread on the surface of each sliding portion. It is also preferable to dispose a slide bearing on each sliding portion (contacting surface). Accordingly, it is possible to reduce friction of the sliding portions, which appropriately prevents noise and abrasion, and what is more, it is possible to move the first cover portion 41 and the second cover portion 42 more smoothly without causing rattles and vibrations.

Moving distances of the first cover portion 41 in the upward-downward direction and the rightward-leftward direction substantially accords with moving distances of the measurement head 14 in the upward-downward direction and the rightward-leftward direction. The measurement head 14 moves up and down depending on a distance between the base 11 and the chin rest 15 in the upward-downward direction and a distance between the chin rest 15 and the subject's eye E in the upward-downward direction. In the ophthalmologic apparatus 10 that acquires eye information of one subject's eye E on the right or left and then acquires eye information of the other, the measurement head 14 moves from the position of one subject's eye E to the position of the other in the rightward-leftward direction. In other words, since the measurement head 14 moves within at least an interpupillary distance PD between right and left subject's eyes E, the first cover portion 41 also moves together with the second cover portion 42 within a moving distance corresponding to the interpupillary distance PD.

In view of the above configuration, the opening 31 is opened not to hinder the movement of the first cover portion 41 within the moving distances in the upward-downward direction and the rightward-leftward direction. The base plate 43 of the first cover portion 41 has a size (surface area) large enough to close the opening 31 constantly even when the base plate 43 moves up and down and from side to side within the moving distances.

Figure 3:
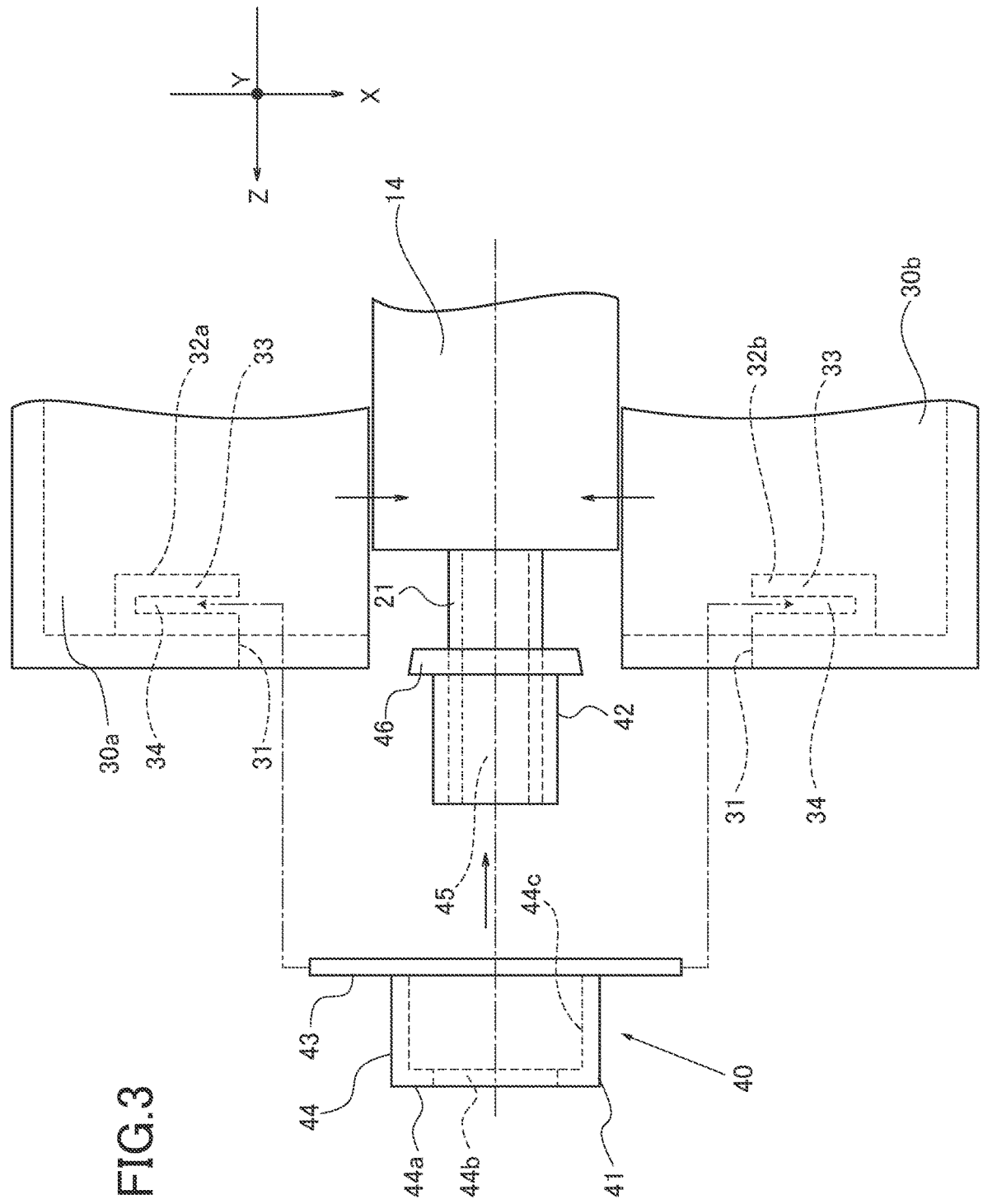
FIG. 3 is a view for describing a process for assembling the cover and the casing.

The procedure for assembling the cover 40 and the casing 30 having the aforementioned configuration will be described with reference to FIG. 3. FIG. 3 is a plan view of the cover 40 and the casing 30 as viewed from the upper side, describing the procedure for assembling the cover 40 and the casing 30. As illustrated in FIG. 3, the casing 30 includes two right and left parts (casings 30a and 30b), and the engagement holder 32 is also divided into two right and left parts (engagement holders 32a and 32b) and fixed to inner surfaces of the casings 30a and 30b. The two casings 30a and 30b are disposed around the device body 20 from both sides and are connected to each other by a fitting structure such as a recess and a protrusion or by a fixing member such as a screw, thereby covering the device body 20. Note that the casing 30 is not limited to this configuration and may have any configuration as long as the casing 30 holds the first cover portion 41.

First, as illustrated in FIG. 3, in the device body 20 having the drive unit 12, the mount 13, the measurement head 14, the control unit 19, and the like assembled on the base 11, the second cover portion 42 is attached to the outer periphery of the objective optical system unit 21 of the measurement head 14. Next, the first cover portion 41 is moved from the front to the rear of the second cover portion 42, and the first cover portion 41 is disposed in the outer periphery of the second cover portion 42. At this time, the second cover portion 42 is inserted into the guide 44 of the first cover portion 41, and one end of the second cover portion 42 projects from the insertion hole 44b.

Next, the two casings 30a and 30b are attached to the device body 20 from both sides, and the base plate 43 of the first cover portion 41 is engaged with the engagement holders 32a and 32b. The two casings 30a and 30b are coupled to each other, thereby completing the attachment of the cover 40 to the casing 30. Since the casing 30 and the cover 40 are assembled with such a structure, the first cover portion 41 is held by the casing 30 while being fixed to the casing 30, which appropriately prevents the first cover portion 41 from moving back and forth and from falling off the casing 30. In addition, the functions of the inward flange 44a and the outward flange 46 prevent the second cover portion 42 from falling off the first cover portion 41.

The process for disassembling these components is opposite to the assembly. First, the casings 30a and 30b are uncoupled and detached from the device body 20. Next, the first cover portion 41 is moved forward and detached from the second cover portion 42, and then, the second cover portion 42 is moved forward and pulled out from the tip of the objective optical system unit 21. In this manner, the cover 40 and the casing 30 are assembled and disassembled easily.

Hereinafter described are functions and effects of the cover 40 when acquiring eye information with the ophthalmologic apparatus 10 having the aforementioned configuration. First, a subject P puts his/her head on the head rest 16 and his/her chin on the chin rest 15 to oppose the ophthalmologic apparatus 10. Next, an examiner operates the operation unit 17 to select a subject's eye E from which eye information is to be acquired and gives an alignment instruction. The control unit 19 receives instruction signals and drives the drive unit 12 to move the measurement head 14 up and down and from side to side, thereby aligning the measurement head 14 in the upward-downward direction and the rightward-leftward direction. At this time, following the movement of the measurement head 14, the objective optical system unit 21 and the second cover portion 42 and the first cover portion 41 housing the objective optical system unit 21 move up and down and from side to side within the opening 31 of the casing 30. Accordingly, the opening 31 is constantly covered with the first cover portion 41, and the subject P does not visually recognize the movement of the measurement head 14 inside the casing 30.

Furthermore, the control unit 19 moves the measurement head 14 back and forth to align in the forward-rearward direction. The objective optical system unit 21 and the second cover portion 42 move back and forth inside the first cover portion 41, following the movement of the measurement head 14, but the first cover portion 41 engaged with the engagement holder 32 of the casing 30 does not move back and forth and keeps covering the opening 31. Accordingly, the subject P does not visually recognize the movement of the measurement head 14 in the forward-rearward direction. This makes it possible for the subject P to concentrate on the acquisition of the eye information without feeling a sense of fear that the measurement head 14 is approaching the subject's eye E.

On completion of the alignment, the control unit 19 receives a measurement instruction from the examiner through the operation unit 17 or automatically controls the measurement head 14 so as to acquire the eye information of the subject's eye E. Since the subject P can concentrate on the acquisition of the eye information, it is possible to acquire the eye information appropriately and efficiently. In addition, the cover 40 attached to the opening 31 appropriately prevents dirt, dust, and foreign matters from penetrating into the opening 31 and prevents a finger or the like from entering the opening 31 by mistake.

Accordingly, it is possible to provide the ophthalmologic apparatus 10 and the cover 40 that appropriately hide the movement of the measurement head 14 as the eye information acquisition unit and appropriately acquire information of a subject's eye. Furthermore, the cover 40 having such excellent effects is formed by a simple configuration including the first cover portion 41 and the second cover portion 42. Accordingly, it is possible to provide the cover 40 that is easy to assemble and disassemble.

Modification

Figure 4A:
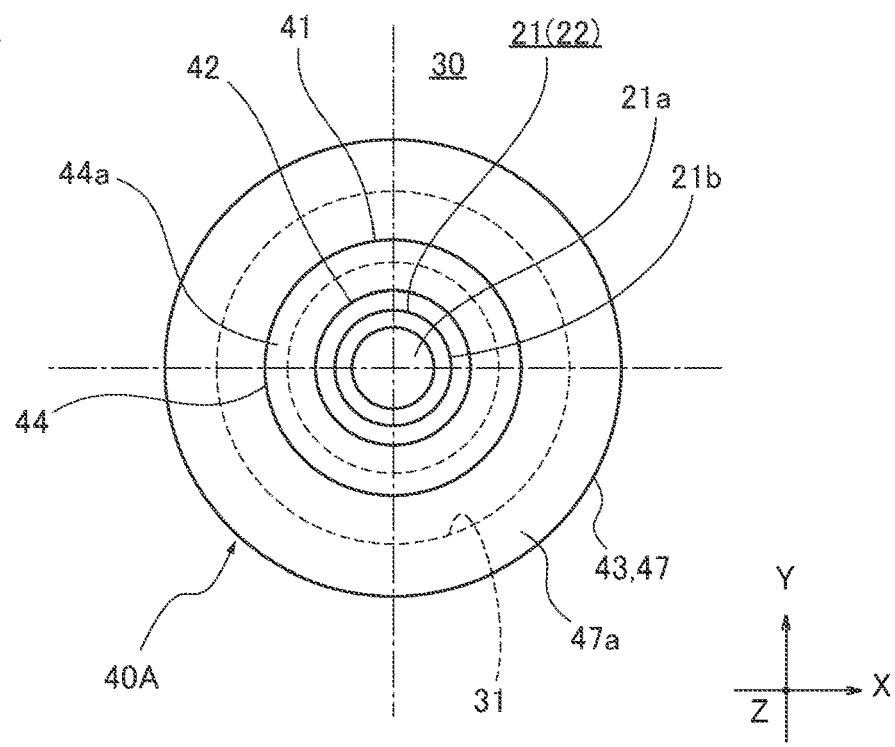
FIGS. 4A and 4B are views for describing configurations of a cover and a casing according to a first modification.
Figure 4B:
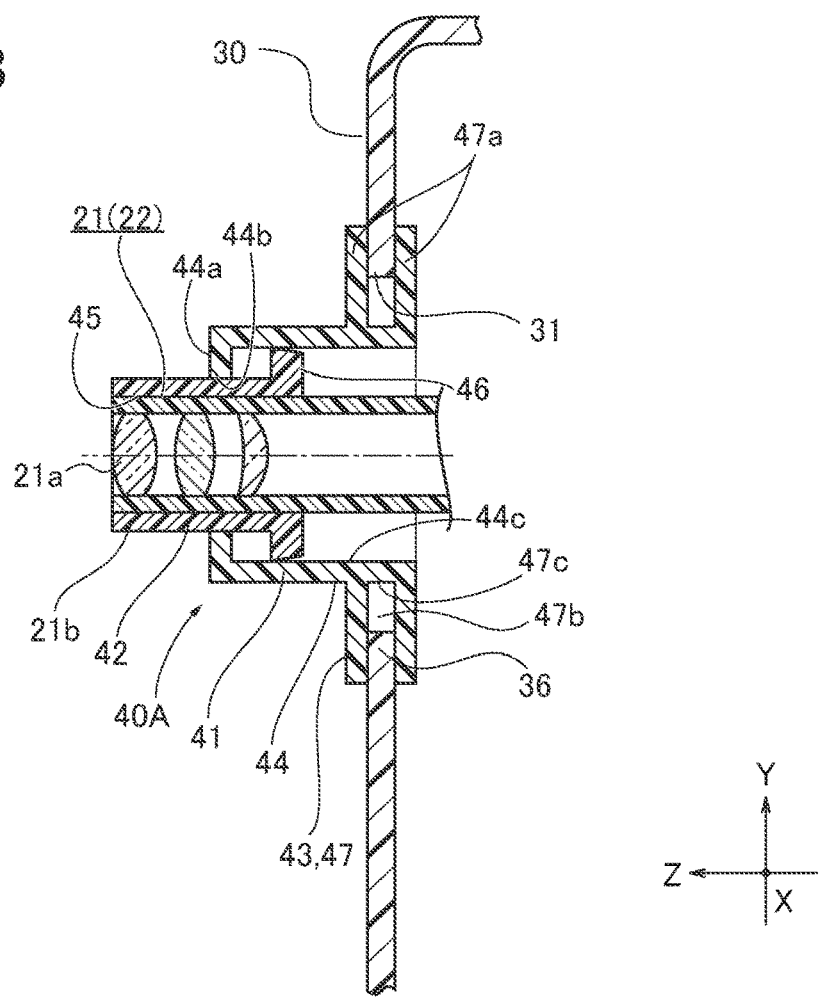
Figure 5A:
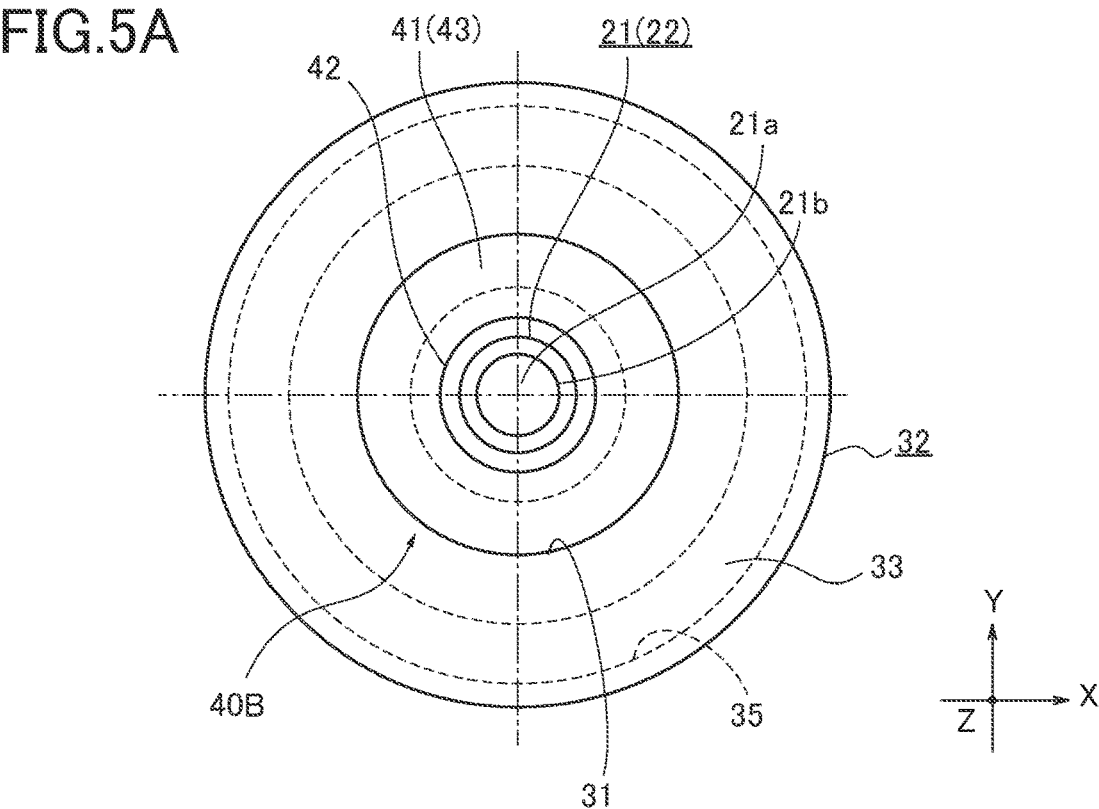
FIGS. 5A and 5B are views for describing configurations of a cover and a casing according to a second modification.
Figure 5B:
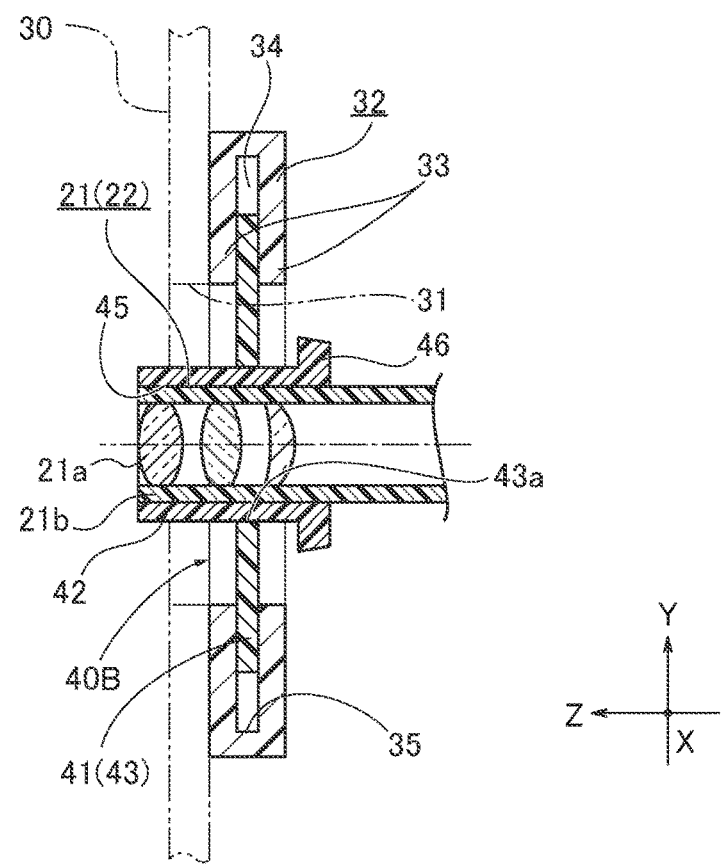
Figure 6A:
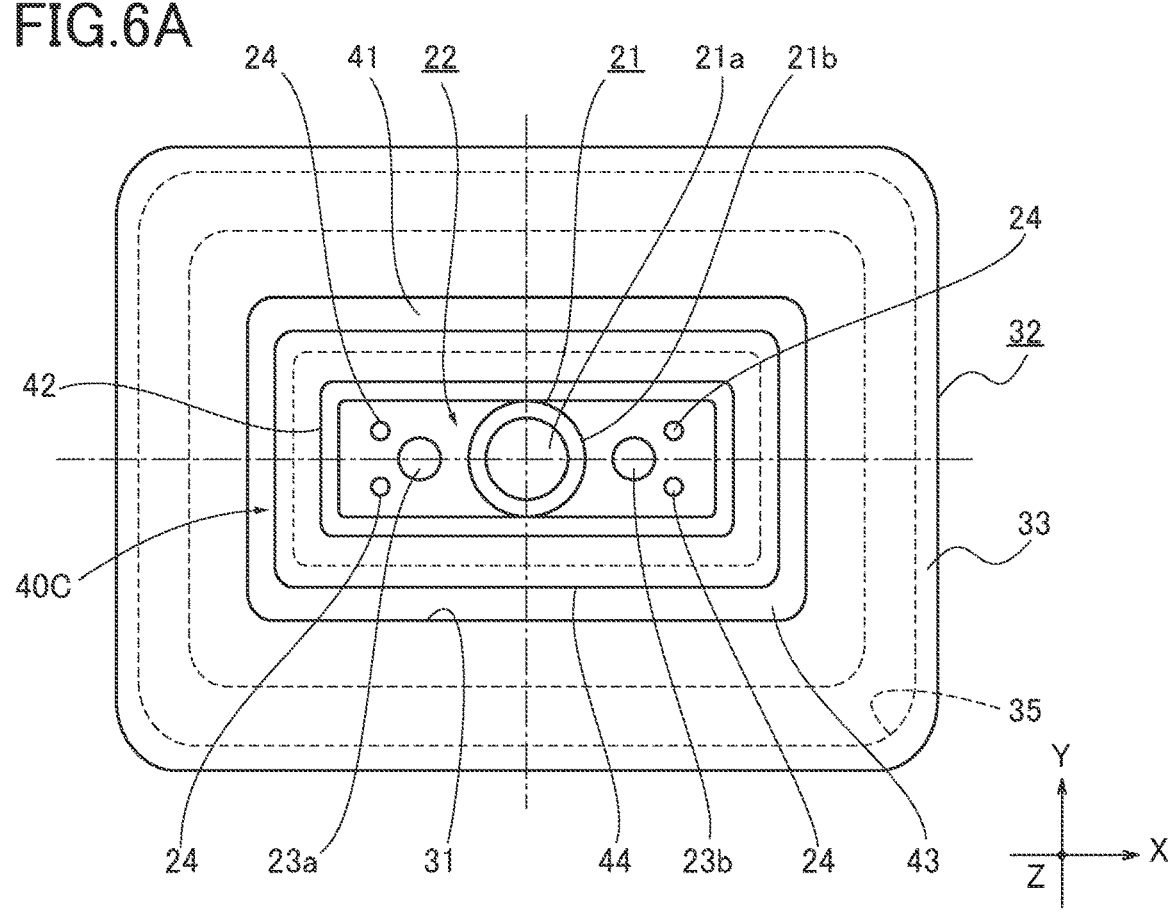
FIGS. 6A and 6B are views for describing configurations of a cover and a casing according to a third modification.
Figure 6B:
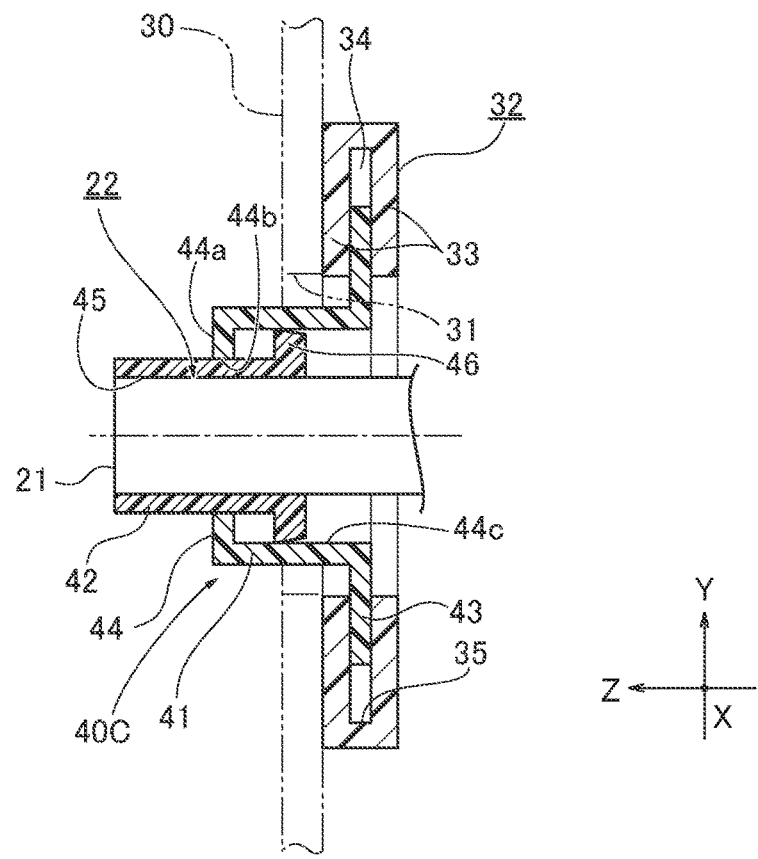

Next, covers 40A to 40C of first to third modifications will be described with reference to FIGS. 4A to 6B. FIGS. 4A, 5A, and 6A are front views of the vicinity of the covers 40A to 40C, and FIGS. 4B, 5B, and 6B are side views (cross-sectional views) thereof. The covers 40A to 40C of the first to third modifications are basically similar to the cover 40 of the first embodiment, each including a first cover portion 41 and a second cover portion 42. Components similar to those in the first embodiment will be denoted by the same reference numerals as those in the first embodiment, and detailed description thereof will be omitted. Hereinafter described are configurations different from the first embodiment.

First, the cover 40A of the first modification illustrated in FIGS. 4A and 4B will be described. In the cover 40 of the first embodiment, the base plate 43 is used as an engagement portion, and the casing 30 includes the engagement holder 32 to be engaged with the base plate 43. On the other hand, in the cover 40A of the first modification, a wall around a peripheral edge of an opening 31 of a casing 30 functions as an engagement portion 36, and an engagement holder 47 that engages with the engagement portion 36 is disposed on a base plate 43. The base plate 43 of the first modification includes two disk-shaped holding walls 47a arranged at an interval substantially equal to a thickness of the wall of the casing 30 in the forward-rearward direction, and a space between the holding walls 47a is used as a housing space 47b that houses (engages with) the engagement portion 36.

In the first modification, the second cover portion 42 and the first cover portion 41 housing the objective optical system unit 21 both move up and down and from side to side, following the movement of the measurement head 14 in the upward-downward direction and the rightward-leftward direction. At this time, the first cover portion 41 moves within the opening 31 along the engagement portion 36 while holding the engagement portion 36. In addition, an outer periphery (a bottom face 47c) of a guide 44 abuts a peripheral edge of the engagement portion 36 inside the housing space 47b so as to suppress the movement of the first cover portion 41. The movement of the first cover portion 41 in the forward-rearward direction is suppressed by the engagement between the engagement portion 36 and the holding walls 47a of the engagement holder 47, and the second cover portion 42 housing the objective optical system unit 21 moves back and forth. Accordingly, the cover 40A of the first modification can also exert effects similar to those of the first embodiment, and the structure around the opening 31 of the casing 30 can be made simpler.

In the cover 40B of the second modification illustrated in FIGS. 5A and 5B, the first cover portion 41 is composed of a disk-shaped base plate 43. The base plate 43 is engaged with an engagement holder 32 of a casing 30, being capable of moving up and down and from side to side. The second cover portion 42 is inserted into an insertion hole 43a disposed in the base plate 43, being relatively movable in the forward-rearward direction. The second modification also offers functions and effects similar to those of the first embodiment and provides the cover 40B having a simpler configuration.

The cover 40C of the third modification illustrated in FIGS. 6A and 6B is used in an ophthalmologic apparatus including stereo cameras (imaging units) 23a and 23b that acquire images of a subject's eye E for alignment. In this ophthalmologic apparatus, a measurement optical system 22 housed in a measurement head 14 includes optical elements such as an objective optical system unit 21, a lens, and an imaging element and also includes the stereo cameras 23a and 23b and light sources 24 for illumination. A total of four light sources 24 are disposed in pairs near the stereo cameras 23a and 23b.

In the cover 40C of the third modification, the second cover portion 42 is a rectangular tubular member having a rectangular shape elongated in the rightward-leftward direction in plan view as illustrated in FIG. 6A so as to house all of the objective optical system unit 21, the stereo cameras 23a and 23b, and the four light sources 24. The second cover portion 42 is not limited to the rectangular tubular member and may be, for example, an elliptical cylindrical member having an elliptical or oval shape in plan view. The second cover portion 42 may have an appropriate shape according to, for example, design or angles of view and arrangements of the stereo cameras 23a and 23b.

Furthermore, in the first cover portion 41 through which the second cover portion 42 is inserted, a guide 44 is a rectangular tubular member including a rectangular insertion hole 44b, and a base plate 43 is formed into a rectangular shape. Still further, an engagement holder 32 with which the base plate 43 is engaged and an opening 31 are formed into a rectangular shape but are not limited thereto. According to moving distances of the measurement head 14 in the upward-downward direction and the rightward-leftward direction, these members may have a shape or size that appropriately covers the opening 31 without hindering the movement of the objective optical system unit 21 and the stereo cameras 23a and 23b. The cover 40C of the third modification may also include the engagement holder 47 as in the first modification or may include the first cover portion 41 composed of the base plate 43 as in the second modification.

The cover 40C of the third modification houses the objective optical system unit 21, the stereo cameras 23a and 23b, and the four light sources 24 but is not limited thereto. For example, similarly to the second cover portion 42 of the first embodiment, the cover 40C may be a cylindrical member and house the objective optical system unit 21. In this case, an inward flange 44a or the base plate 43 of the first cover portion 41 is provided with openings on the right and left sides of an insertion hole 44b so that the stereo cameras 23a and 23b and the light sources 24 can be seen through the openings. A glass plate for preventing penetration of dust and the like is desirably disposed in the openings. Even with such a configuration, the first cover portion 41 and the second cover portion 42 move up and down and from side to side together with the objective optical system unit 21, the stereo cameras 23a and 23b, and the light sources 24. In addition, even when the objective optical system unit 21, the stereo cameras 23a and 23b, and the light sources 24 move back and forth relative to the first cover portion 41, the openings are located on optical paths (on optical axes) of the stereo cameras 23a and 23b. Accordingly, it is possible to capture images of the subject's eye E by the stereo cameras 23a and 23b through the openings of the first cover portion 41.

Although the ophthalmologic apparatus of this disclosure is described based on the embodiment and modifications, the specific configuration is not limited by these embodiment and modifications. Changes or additions of the design are allowed without departing from the gist of the disclosure according to the claims.

For example, in the above embodiment and modifications, the measurement head 14 moves up and down, from side to side, and back and forth, but the measurement head 14 may be configured to rotate about an axis parallel to Y-axis. Such a configuration makes it possible to acquire eye information of a subject's eye E not only from the front but also from a desired angle. In addition, the measurement head 14 may be configured to move in any one direction or two directions of the upward-downward direction, the rightward-leftward direction, and the forward-rearward direction.

In the embodiment, the monitor 18 is rotatable by the rotary support mechanism 18b, but the present invention is not limited thereto. For example, the monitor 18 may be fixed to the casing 30 in a non-rotatable manner. Furthermore, the monitor 18 may be detachable from the casing 30 and may be connected to the control unit 19, enabling transmission and reception of data by short-range wireless communication such as Wi-Fi (registered trademark) or Bluetooth (registered trademark).

What is claimed is:

1. An ophthalmologic apparatus comprising:
   a device body; and
   a casing covering the device body,
   wherein the device body comprises:
      an eye information acquisition unit including an objective optical system configured to oppose an eye of a subject, and to acquire information of the eye of the subject;
      a drive unit configured to move the eye information acquisition unit relative to the subject's eye in an upward-downward direction, a rightward-leftward direction, and a forward-rearward direction perpendicular to each other; and
      a control unit configured to control the eye information acquisition unit and the drive unit, and
   wherein the casing comprises a casing body, an opening on one surface of the casing body opposing the eye of the subject, and a cover configured to cover the opening, the cover including:
      a first cover portion movable relative to the casing body in the upward-downward direction and the rightward-leftward direction, and disposed in the opening so as not to be movable in the forward-rearward direction; and
      a second cover portion attached to an outer periphery of the objective optical system and inserted into the first cover portion, and configured to be movable relative to the first cover portion in the forward-rearward direction.

2. The ophthalmologic apparatus according to claim 1, further comprising:
   an engagement portion in a first one of the opening of the casing body and the first cover portion; and
   an engagement holder a second one of the opening and the first cover portion,
   wherein the engagement portion and the engagement holder are configured to allow the first cover portion to move in the upward-downward direction and the rightward-leftward direction within a predetermined moving distance, and to prevent the first cover portion from moving in the forward-rearward direction while the first cover portion is attached and fixed to the casing.

3. The ophthalmologic apparatus according to claim 1, wherein the first cover portion includes:
   a base plate in the opening; and
   a guide projecting from the base plate toward the eye of the subject and configured to guide the second cover portion to move in the forward-rearward direction.

4. The ophthalmologic apparatus according to claim 3, wherein the second cover portion includes an outward flange projecting radially outward and located between an outer surface of the second cover portion and an inner surface of the guide at an end facing the casing.

5. The ophthalmologic apparatus according to claim 1, wherein the eye information acquisition unit includes two or more imaging units configured to capture an image of the eye of the subject from different directions, and the second cover portion is attached to an outer periphery of the two or more imaging units and the objective optical system.

6. The ophthalmologic apparatus according to claim 1, further comprising a friction reducer configured to reduce frictional resistance on at least one of a first contacting surface between the casing and the first cover portion and a second contacting surface between the first cover portion and the second cover portion.

7. A cover in an opening of a casing body of a casing of an ophthalmologic apparatus having an eye information acquisition unit including an objective optical system configured to oppose an eye of a subject, the eye information acquisition unit being configured to acquire information of the eye of the subject and to be movable relative to the eye of the subject in an upward-downward direction, a rightward-leftward direction, and a forward-rearward direction perpendicular to each other, wherein the cover comprises:
- a first cover portion movable relative to the casing body of the casing in the upward-downward direction and the rightward-leftward direction, and disposed in the opening so as not to be movable in the forward-rearward direction; and
- a second cover portion attached to an outer periphery of the objective optical system and inserted into the first cover portion, and configured to be movable relative to the first cover portion in the forward-rearward direction.

* * * * *